United States Patent [19]

El-Chahawi et al.

[11] 3,980,697
[45] Sept. 14, 1976

[54] BUTYRIC ACID ESTERS

[75] Inventors: Moustafa El-Chahawi, Troisdorf; Uwe Prange, Neiderkassel-Ranzel; Hermann Richtzenheim, Much-Schwellenbach; Wilhelm Vogt, Cologne-Sulz, all of Germany

[73] Assignee: Dynamit Nobel Aktiengesellschaft, Cologne, Germany

[22] Filed: Jan. 24, 1975

[21] Appl. No.: 544,022

[30] Foreign Application Priority Data

Feb. 1, 1974 Germany.......................... 2404776

[52] U.S. Cl. ...................... 260/484 R; 260/486 AC
[51] Int. Cl.² .......................................... C07C 69/66
[58] Field of Search ................. 260/484 R, 486 AC

[56] References Cited
UNITED STATES PATENTS

| | | | |
|---|---|---|---|
| 3,338,961 | 8/1967 | Closson et al. ........... | 260/544 |
| 3,457,299 | 7/1969 | Closson et al. ........... | 260/486 |
| 3,636,082 | 1/1972 | Knowles.................... | 260/475 R |

*Primary Examiner*—Paul J. Killos
*Attorney, Agent, or Firm*—Burgess, Dinklage & Sprung

[57] ABSTRACT

Butyric acid esters of the formula:

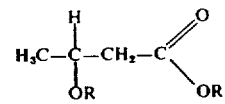

wherein each R is alkyl, alkyl having an alkoxy substituent, or cycloalkyl, and the R's are the same. The esters are prepared by contacting an allyl halide with carbon monoxide, an alcohol of the formula ROH wherein R is as above, and an alkali alcoholate of the same alcohol, in the presence of a catalyst for the reaction at a pH of 10–14. The esters are useful as solvents for polymers and as plasticizers.

19 Claims, No Drawings

BUTYRIC ACID ESTERS

The reaction takes place in accordance with the following equation:

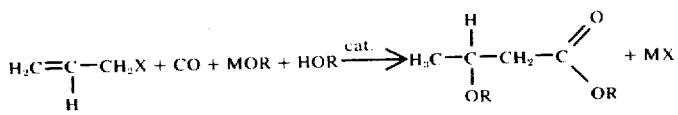

BACKGROUND

The present invention relates to a method of preparing β-alkoxybutyric acid alkyl esters by the reaction of allyl halides with carbon monoxide, alkali alcoholates and alcohols in the presence of catalysts.

It is known to prepare vinyl acetic acid methyl esters plus small amounts of crotonic acid methyl esters from allyl halides with carbon monoxide and methanol in the presence of catalytic amounts of nickel carbonyl and thiourea, at atmospheric pressure, at a temperature between 15 and 35°C, and at a pH between 5.5 and 9 (German "Offenlegungsschrift" No. 1,936,725).

It is furthermore known that palladium chloride catalyzes the carbonylation of allyl chloride. In the presence of an inert solvent such as benzene, vinyl acetyl chloride forms; in an alcohol as solvent, the corresponding vinyl acetic acid esters form. Crotonic acid chloride or crotonic acid esters occur as by-products due to isomerization of the double bond (J. Tsuji, J. Kiji, S. Imanura and M. Morikawa, J. Amer. Chem. Soc. 86, 4350 (1964) and D. Medema, R. Van Helden and C. F. Kohll, Inorg. Chem. Acta, 3, 255 (1969)).

Disadvantages of these processes lie in the necessity of using carbon monoxide in the 100 kp/cm² pressure range, and in the unfavorable weight ratio of the allyl halide to palladium chloride, long reaction times or low yields, and reactions performed in a plurality of stages. π-allyl metal complex compounds are formed as intermediates in the carbonylation of allyl halides, namely bis-π-allyl nickel bromide and π-allyl palladium bromide, which by reaction with CO and methanol produce vinyl acetic acid or crotonic acid methyl ester, respectively (Z. Naturforschung 17b (1962) 484 and 850), or, in the latter case, by reaction with CO and ethanol, have produced vinyl acetic acid ethyl ester (Tetrahedron Letters 26 (1963) 1811).

Furthermore, β-alkoxybutyric acid alkyl esters can by prepared from crotonic acid esters and alcohol under the catalytic influence of alkali alcoholates (Ullmann (1960), Vol. 5, p. 617).

THE INVENTION

It has been found that the preparation of β-alkoxybutyric acid alkyl esters can be performed in a one-step process by the reaction of allyl halides with carbon monoxide, alcohol in the presence of an alkali alcoholate that is the basis of the alcohol, and catalytic amounts of e.g. nickel carbonyl or cobalt carbonyl or a catalyst system consisting of $CoCl_2 \cdot 6 H_2O$, manganese powder and $Na_2S_2O_4$.

The subject matter of the invention is a process for the preparation of β-alkoxybutyric acid alkyl esters, which is characterized by the reaction of an allyl halide with carbon monoxide, an alcohol, an alkali alcoholate of the same alcohol, and catalytic amounts of metal carbonyls or of a catalyst system containing cobalt, in a pH ranging from 10 to 14.

In this equation, R represents a primary, secondary or tertiary alkyl radical having 1 to 8 carbon atoms or the cyclohexyl radical, X represents the halogens chlorine, bromine, or iodine, and M represents an alkali metal, preferably sodium or potassium.

Important advantages of the invention are the following:

1. The β-alkoxybutyric acid alkyl esters can be prepared in one reaction step from allyl halides.
2. No additions of thiourea to nickel carbonyl and cobalt carbonyl catalysts are necessary, so that the products are not impaired by the bad odor created by compounds containing sulfur.
3. A great number of alcohols and corresponding alcoholates are usable as reaction components, and
4. High yields of β-alkoxybutyric acid alkyl esters can be achieved.

Surprisingly, the four reactants react quite uniformly, for the most part, in accordance with the reaction equation to produce high yields.

The reaction is performed by adding alkali alcoholate solution and an allyl halide drop by drop to an alcoholic solution of the metal carbonyl or suspension of the catalyst system, such that an excess of alkali alcoholate with respect to allyl halide is always present. The reaction can best be followed with a glass electrode and a pH meter, it being important to have a pH of 10 to 14 in the reaction solution. Since the pH is measured in a non-aqueous solution, the pH values given by the pH meter do not have to be completely the same as the actual pH values of aqueous solutions. The pH values herein are the meter readings in the reaction mediums hereof.

Suitable alcohols are univalent alcohols, which can be straight-chained or branched, and can in some cases have an alkoxy substituent with 1 to 2 carbon atoms; examples are methanol, ethanol, propanol, isopropanol, n-butanol, isobutanol, tertiary butanol, n-pentanol, 2-ethylhexanol, cyclohexanol or methyl glycol. They are used in a 2 to 20-fold excess with respect to the allyl halide.

For 1 mole of allyl halide at least 1 mole of alkali alcoholate is required, but an excess of about 10% of the alkali alcoholate is better, so as to assure a pH greater than 10. The preferred alkali alcoholates are the sodium and potassium alcoholates of the above-described alcohols.

The reaction of the named reactants is performed in a temperature range from 0° to 100°C, preferably from 10° to 60°C. The reaction time will amount to from 1 to 10 hours according to the temperature selected.

The reaction of the allyl halides takes place at a pressure between 0.5 and 5 atmospheres, preferably between 1.0 and 4 atmospheres. Higher pressures are possible, but not necessary.

Carbonyls of nickel or cobalt can be used as catalysts, or a catalyst system of $CoCl_2 \cdot 6 H_2O$, powdered manganese and $Na_2S_2O_4$.

The molar ratio of catalyst to allyl halide can be between 1 : 10 and 1 : 500, but will be preferably between 1 : 15 and 1 : 200.

Allyl chloride, allyl bromide or allyl iodide can be used as the allyl halide. The chloride is preferred because it is easily available.

The β-alkoxybutyric acid alkyl esters having alkyl groups of low carbon number are suitable as solvents for polymers such as acrylic-or vinyl polymers, while those of higher carbon numbers are suitable for use as plasticizers on account of their higher boiling points, for e.g. vinyl polymers.

β-(2-ethyl-hexoxy)-butyric acid-2-ethylhexyl ester (Example 6) is useful as plastiziser for e.g. polyvinyl butyral.

β-(2-methoxy ethoxy)-butyric acid-2-methoxyethyl ester (Example 10) is useful as plastiziser for e.g. polyvinyl acetate.

SUMMARY

Thus the invention provides butyric acid esters of the formula:

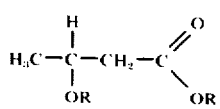

wherein each R is alkyl, alkyl having an alkoxy substituent, or cycloalkyl, and the R's are the same. The esters can be prepared by contacting an allyl halide with carbon monoxide, an alcohol of the formula ROH wherein R is as above, and an alkali alcoholate of the same alcohol at a temperature and pressure and for a time sufficient for reaction thereof to produce said butyric acid ester, in the presence of a catalyst for the reaction, at a pH of 10 – 14.

EXAMPLES

In the following examples, unless otherwise indicated, a solution of the catalyst in 200 ml of the alcohol is charged to the reaction vessel. Carbon monoxide is added to a pressure of about 1.8 atmospheres and a 20% solution of the alkali alcoholate in the alcohol is added to adjust the pH to about 12. The pH is monitored with the meter described in Example 1. Then, allyl chloride and a 20% solution of the alkali alcoholate in the alcohol are added drop by drop so that the pH remains between 10 and 14. The alkali alcoholate is used in 10% molar excess with respect to the allyl chloride. Carbon monoxide is added during the reaction to maintain a pressure of about 1.8 atmospheres. The weight % catalyst (e.g. Example 2) is on the basis of allyl chloride.

EXAMPLE 1

In a 1-liter reaction vessel provided with stirrer, two dropping funnels, condenser, gas introduction tube and a glass electrode filled with a saturated methanolic solution of lithium chloride and joined through a diaphragm to a thalamide reference electrode, 2.0 ml of $Ni(CO)_4$ in 200 ml of methanol is charged. The vessel is purged with carbon monoxide and a pressure of 1.8 atmospheres is established. At a temperature of 40°C, first a part of a 20% sodium methylate solution is added drop by drop until the pH meter gives a reading of about 12. Then over a period of 4 hours, 76.5 g (1 mole) of allyl chloride and 297 g of 20% sodium methylate solution in methanol, which contains 1.1 mol sodium methylat are added drop by drop such that the pH remains between 11 and 12. The sodium methylate is used in a 10% excess with respect to the allyl chloride. During the reaction carbon monoxide is fed in to the extent that a pressure of 1.8 atmospheres is maintained. When the addition of the components has ended, the mixture is stirred for 2 more hours at 40°C, and then let cool to room temperature. The reaction mixture is filtered from the precipitated sodium chloride and distilled. Distillation yields 10.2 g of crotonic acid methyl ester (10.7% yield) and 98 g of β-methoxybutyric acid methyl ester (78% yield) at a transformation of 95.2% of the allyl chloride. Also, traces can be detected of vinyl acetic acid methyl ester, allyl methyl ether and 1,5-hexadiene.

EXAMPLE 2

Under the same conditions as in Example 1, but with the use of varying amounts of nickel carbonyl, the results listed in Table 1 are obtained.

Table 1

| Wt.-% $Ni(CO)_4$ | 0.85 | 1.71 | 3.5 | 8.6 |
|---|---|---|---|---|
| Allyl chloride transformation | 58.8% | 79.4% | 85.0% | 95.0% |
| Yield of β-methoxybutyric acid methyl ester | 72.5% | 85.0% | 89.0% | 92.0% |
| Yield of crotonic acid methyl ester |  | — | 7.0% | 2.6% |

EXAMPLE 3

Under the same conditions as in Example 1, but with varying temperatures, the results given in Table 2 are obtained using 8.6 wt.-% $Ni(CO)_4$ per batch.

Table 2

| Temperature °C: | 20° | 40° | 60° |
|---|---|---|---|
| Reaction time (hours) | 10 | 6 | 4 |
| Allyl chloride transformation | 100.0% | 95.0% | 95.8% |
| Yields: | | | |
| β-methoxybutyric acid methyl ester | 94.5% | 92.0% | 89.3% |
| Crotonic acid methyl ester | 2.5% | 2.6% | 3.0% |

EXAMPLE 4

121 g (1 mole) of allyl bromide is reacted as described in Example 1 at 30°C with 5 ml of nickel carbonyl as catalyst over a period of 5-½ hours, the pH ranging from 10.5 to 11.9. The distillation of the reaction product yields 4 g of crotonic acid methyl ester (yield 4%) and 118.5 g of β-methoxybutyric acid methyl ester (yield 90%).

EXAMPLE 5

In a manner similar to Example 1, but in a 2-liter reaction vessel, 153 g (2 moles) of allyl chloride is reacted with 960 g (2.1 moles) of 15% sodium ethylate solution and 5 ml of nickel carbonyl at 60°C for 7 hours. Distillation yields 221.5 g of β-ethoxybutyric acid ethyl ester (yield 70%) plus 34 g of crotonic acid ethyl ester (yield 15%) at a transformation of 98.2%. Ethanol is used in place of methanol.

EXAMPLE 6

β-(2-ethyl-hexoxy)-butyric acid-2-ethylhexyl ester.

In a manner similar to Example 1, but in a 10-liter reaction vessel, 230 g (3 moles) of allyl chloride is reacted with 3.2 kg (3.3 moles) of 15.5% sodium-2-ethylhexylate in the presence of 10 ml of nickel carbonyl at 60°C and 1.2 atmospheres for a period of 8 hours. Upon distillation, 875 g of β-(2-ethylhexoxy)-butyric acid-2-ethylhexyl ester is obtained (yield 89%). This substance has a boiling point at 2 Torr ($BP_2$) of 160°C and an index of refraction at 20°C of $n_D^{20}$ = 1.4410. The NMR spectrum in carbon tetrachloride with tetramethylsilane as the internal standard shows, at $\delta$ = 0.91 ppm, triplets, $\delta$ = 1.14 ppm and $\delta$ = 1.3 ppm, doublet and multiplet, $\delta$ = 2.34 ppm, AB system ($-CH_2-COO-$), $\delta$ = 3.27 ppm, AB system ($-O-CH_2-$, ether) and $\delta$ = 3.94 doublet ($-O-CH_2-$, ester), in the relative integration ratio of 12 : 20.9 : 2.0 : 1.8 : 1.0 : 1.6.

Combustion analysis gives the following values: $C_{20}H_{40}O_3$ (molecular wt.: 328.56 ). Found: C = 72.9%; H = 12.3%. Calculated: C = 73.11%; H = 12.27%

EXAMPLE 7

38.3 g (0.5 mole) of allyl chloride is reacted in the apparatus described in Example 1, under the reaction conditions specified therein, with 5 g of cobalt carbonyl as catalyst and 0.55 mole of 20% sodium methylate solution. After separation and distillation 11 g is obtained of β-methoxybutyric acid methyl ester (20% yield at an 85% transformation of allyl chloride). The main product is allyl methyl ether.

EXAMPLE 8

A catalyst system consisting of 5 g of $CoCl_2 \cdot 6 H_2O$, 5 g of manganese powder and 1 g of $Na_2S_2O_4$, is stirred in 200 ml of $CH_3OH$ at 40°C and 1.8 atmosphere of CO, a slight absorption of CO being observed. Then 1.1 mole of sodium methylate solution and 76.5 g (1 mole) of allyl chloride are added drop by drop over a period of 4 hours as in Example 1. Two hours thereafter the reaction is terminated. With a transformation of 70% of the allyl chloride, 10 g of β-methoxybutyric acid methyl ester (yield 11%) plus 5.2 g of crotonic acid methyl ester (yield 7.5%) and 1 g of vinyl acetic acid methyl ester (yield 1.5%) are obtained. The rest of the transformed allyl chloride yields allyl methyl ether.

EXAMPLE 9

46.5 g (1 mole) of allyl chloride is reacted as described in Example 1 at 35°C with 5 ml of nickel carbonyl as catalyst in 280 ml of n-butanol at a CO pressure of 1.5 atmosphere with the addition of 615 g (1.1 mole) of 20 wt.-% potassium n-butylate over a period of 4 hours. The reaction is terminated after 6 hours at pH values of 10.8 to 12.2. The yield is 175 g (= 81%) of β-n-butoxybutyric acid-n-butyl ester plus a small amount of crotonic acid-n-butyl ester.

EXAMPLE 10

β-(2-methoxyethoxy)-butyric acid-(2-methoxyethyl) ester 76.5 g (1 mole) of allyl chloride is reacted as described in Example 1 at 45°C in the presence of 3 ml of nickel carbonyl as catalyst and 300 ml of methyl glycol, at a CO pressure of 1.7 atmospheres, for a period of 5 hours, with 440 g (1.12 moles) of 25% sodium methyl glycolate of the formula $Na-O-CH_2-CH_2-OCH_3$ at a pH between 11.0 and 12.5. 170 g (= 77%) of β-(2-methoxyethoxy)-butyric acid-(2-methoxyethyl) ester having a boiling point of 81°C at 0.3 Torr. The index of refraction at 20°C is 1.4311.

Elemental analysis: $C_{10}H_{20}O_5$ (mol. wt. = 220.26). Calculated: C = 54.53; H = 9.15. Found: C = 54.81; H = 9.20

The NMR spectrum in benzene contains signals at $\delta$ = 1.11 ppm (doublet), $\delta$ = 2.40 ppm

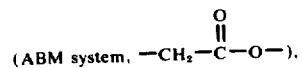

$\delta$ = 3.16 and $\delta$ = 3.2 ppm (singulets, $-O-CH_3$), $\delta$ = 3.3 to 3.54 ppm (multiplet), $\delta$ = 3.86 ppm (sextet) and $\delta$ = 4.15 ppm

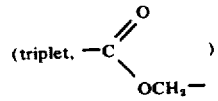

in the relative integration ratio of 2.9 : 1.8 : 5.9 : 6.1 : 1.4 : 2.0.

What is claimed is:

1. Method of preparing butyric acid ester of the formula:

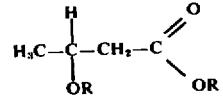

wherein each R is alkyl, alkyl having an alkoxy substituent, or cycloalkyl, and the R's are the same, which comprises contacting an allyl halide with carbon monoxide, and alcohol of the formula ROH wherein R is as above, and an alkali alcoholate of the same alcohol at a temperature and pressure and for a time sufficient for reaction thereof to produce said butyric acid ester, in the presence of a catalyst for the reaction comprising cobalt or metal carbonyl, at a pH of 10 – 14.

2. Method of claim 1, wherein the catalyst is a metal carbonyl.

3. Method of claim 2, wherein the metal carbonyl and allyl halide are used in the molar ratio of 1 : 10 to 1 : 500.

4. Method of claim 1, wherein the catalyst comprises cobalt.

5. Method of claim 1, wherein the catalyst is nickel carbonyl or cobalt carbonyl.

6. Method of claim 1, wherein the catalyst is nickel carbonyl.

7. Method of claim 1, wherein the catalyst is cobalt carbonyl.

8. Method of claim 1, wherein the catalyst is $CoCl_2 \cdot 6H_2O$, Mn powder, and $Na_2S_2O_4$.

9. Method of claim 1, wherein the alkali alcoholate is sodium or potassium alcoholate.

10. Method of one of claim 1, wherein the reaction is performed at a temperature between 0° and 100°C.

11. Method of one of claim 1, wherein the reaction is performed at a carbon monoxide pressure of 0.5 to 5 atmospheres.

12. Method of claim 1, wherein the allyl halide is allyl chloride, bromide or iodide.

13. Method of claim 1, wherein the alcohol is a primary, secondary or tertiary alcohol having 1 to 8 carbon atoms.

14. Method of claim 1, wherein R has 1 to 8 carbon atoms.

15. Method of claim 1, wherein the alkali alcoholate is in stoichiometric excess with respect to the allyl halide.

16. $\beta$-(2-ethyl-hexoxy)-butyric acid-2-ethylhexyl ester.

17. $\beta$-(2-methoxyethoxy)-butyric acid-2-methoxyethyl ester.

18. Method of claim 1, wherein the catalyst is a carbonyl of nickel or cobalt, or the system $CoCl_2 \cdot 6H_2O$, manganese powder and $Na_2S_2O_4$.

19. Method of claim 18, wherein the temperature is 0° to 100°C, and the pressure is 0.5 to 5 atmospheres.

* * * * *